United States Patent [19]

Tarvainen

[11] Patent Number: 5,268,952
[45] Date of Patent: Dec. 7, 1993

[54] MEASURING APPARATUS FOR MEASURING FAULTS IN A PIPELINE

[75] Inventor: Reino Tarvainen, Espoo, Finland

[73] Assignee: Valtion Teknillinen Tutkimuskeskus, Espoo, Finland

[21] Appl. No.: 858,988

[22] PCT Filed: Nov. 22, 1990

[86] PCT No.: PCT/FI90/00282

§ 371 Date: May 21, 1992

§ 102(e) Date: May 21, 1992

[87] PCT Pub. No.: WO91/08470

PCT Pub. Date: Jun. 13, 1991

[30] Foreign Application Priority Data

Nov. 23, 1989 [FI] Finland .................................. 895615

[51] Int. Cl.$^5$ .............................................. G01B 15/06
[52] U.S. Cl. ................................................ 378/59; 378/58
[58] Field of Search ................................. 378/59, 58

[56] References Cited

U.S. PATENT DOCUMENTS

| | | | |
|---|---|---|---|
| 3,158,744 | 11/1964 | Bernstein | 250/360 |
| 4,694,479 | 9/1987 | Bacskai et al. | 378/59 |
| 4,695,729 | 9/1987 | Monno et al. | 378/59 |

FOREIGN PATENT DOCUMENTS

| | | | |
|---|---|---|---|
| 2608841 | 9/1977 | Fed. Rep. of Germany . | |
| 890175 | 12/1981 | U.S.S.R. | 378/59 |

OTHER PUBLICATIONS

Patent Abstracts of Japan, vol. 10, No. 169, p. 468, Abstract of JP 61-22239.

Primary Examiner—Craig E. Church
Attorney, Agent, or Firm—Kane, Dalsimer, Sullivan, Kurucz, Levy, Eisele & Richard

[57] ABSTRACT

A measuring apparatus comprising a gamma radiation or x-ray source (2), two detectors (3,3$^1$) and an output device, for measuring faults in a pipe (1) and for observing foreign objects present in the pipe. A procedure, in particular one for observing faults of a pipe and foreign objects present in a pipe, wherein the measuring apparatus and the pipe (1) are moved relative to each other.

3 Claims, 2 Drawing Sheets

MEASURING APPARATUS FOR MEASURING FAULTS IN A PIPELINE

The present invention concerns a measuring apparatus, and a corresponding procedure, for measuring faults in a pipeline and for observing foreign objects occurring in a pipeline.

Problems in maintenance are at present caused in various installations in processing industry, in power plants and equivalent by the job of monitoring the condition of pipelines. Damage to the pipelines is usually only observed after leakage has already occurred, when the losses thereby incurred may be appreciable indeed.

The object of the invention is to eliminate the drawbacks mentioned above. Specifically, the object of the invention is to create a measuring apparatus, and a corresponding measuring procedure, by the aid of which the condition of pipelines can be monitored whenever desired, without interfering with their use in various processes, and with the aid of which faults in the pipelines can be accurately located.

The measuring apparatus of the invention for measuring pipeline faults comprises on one side of the pipe a gamma radiation or x-ray source and on the other side, two detectors located at a distance of each other in the axial direction of the pipe and aligned with the radiation source, and an output device, the radiation source being disposed to direct measuring beams through the walls of the pipe that is being measured, at an angle relative to each other; the detectors being disposed to detect the beams that have traversed the pipe walls; and the output device being disposed to record a signal characterizing the pipe wall thickness.

In the procedure of the invention, there are directed through the pipe walls, two beams enclosing an angle with each other and traversing the pipe; the beams are moved, one trailing the other, relative to the pipe in the measuring direction; the intensities of the beams that have passed through the pipe walls are measured; and the locations of faults in the pipe are determined by comparing the spacing in the measuring direction of the signals obtained from the beams and the spacing of the beams at both traversing points.

The measuring apparatus and measuring procedure of the invention are based on the fact that two collineated radiations which are moved one after the other pass through the pipe wall with a given spacing when entering the pipe, and when they come out through the mantle on the other side of the pipe their spacing is different, preferably greater. Therefore comparison of the results of measurement obtained from different beams enables inferences to be drawn as to on which side of the pipe and at what location is the measured point of observation, such as e.g. a thinned-down area.

The measuring apparatus and the procedure are based on the fact that the radiation which is being used is absorbed by the pipe mantle in greater proportion, the greater the thickness at the traversing point. It is therefore also possible with the apparatus and procedure of the invention to measure obstructions in the pipe, in addition to various instances of corrosion damage and the like.

The pipes that are being measured may be made of reinforced plastic, steel, aluminium, copper, etc., and they may also be lagged with various lagging materials.

The radiation used in the invention is gamma or x-ray radiation. The wavelength of the radiation is on the order of $10^{-9}$ cm (gamma radiation) and $10^{-9}$ to $10^{-6}$ cm (x-rays). Cs 137 is a particularly well suited radiation source for the measurement.

The radiation that has passed through the pipe walls is detected with detectors on the opposite side of the pipe. For detectors one may use any kind of conventional radiation detectors which are fit for detecting the gamma or x-ray radiation in question. The signals from the detectors may be amplified, and the signals may be output by conventional methods known in the art, with a plotter, on film, on magnetic tape, etc.

Preferably, the radiation from the radiation source is accurately aligned with a collimator before and/or after the pipe that is being measured, so that sharp delimiting of the radiation is achieved.

Although it is feasible to have one of the two radiations perpendicular to the pipe and the other at an angle, it is advantageous if the angle enclosed by the radiation observed by the detectors and the normal on the pipe is within 1° to 60°, suitably 1° to 15°, advantageously 1° to 5°, the radiations being at equal and opposite angles relative to the normal. Hereby the conditions of measurement will be exactly equal for both radiations, and any differences observed in the radiations will signify existing deviations in the structure of the pipe or obstruction present in the pipe.

The distance between detectors is advantageously on the order of 10 to 100 mm, suitably 10 to 60 mm, e.g. 10 to 20 mm.

The beams going to the detectors may be attenuated with filtering plates, to be appropriate for the detectors. Such filtering plates may be inserted in the path either after the radiation source and before the pipe or after the pipe and before the detectors. The material to be used for the filtering plates is a conventional material used to attenuate radiation.

The signals from the detectors may be electrically amplified to be appropriate for the plotter, each channel by itself, whereby the thickness can be read, once the apparatus has been calibrated.

The measurement of the invention is carried out by moving the measuring apparatus and the pipe under measurement relative to each other. This may be done either by moving the measuring apparatus relative to the stationary pipe or by moving the pipe relative to the stationary measuring apparatus.

The measurement of the invention is advantageously performed as a null balance measurement in that the radiations to be measured are continuously compared with each other and only when the radiation intensities differ, the magnitude of the difference and its location in the pipeline are recorded in any convenient manner.

The advantage of the invention over prior art is that it affords a rapid, accurate and simple way of measurement without any interference with the operation of the pipelines.

The invention is described in the following in detail with the aid of examples, referring to the attached drawings, wherein:

FIG. 1 presents a schematic diagram of an apparatus according to the invention,

FIG. 2 presents an arrangement according to the invention,

Figure 1:
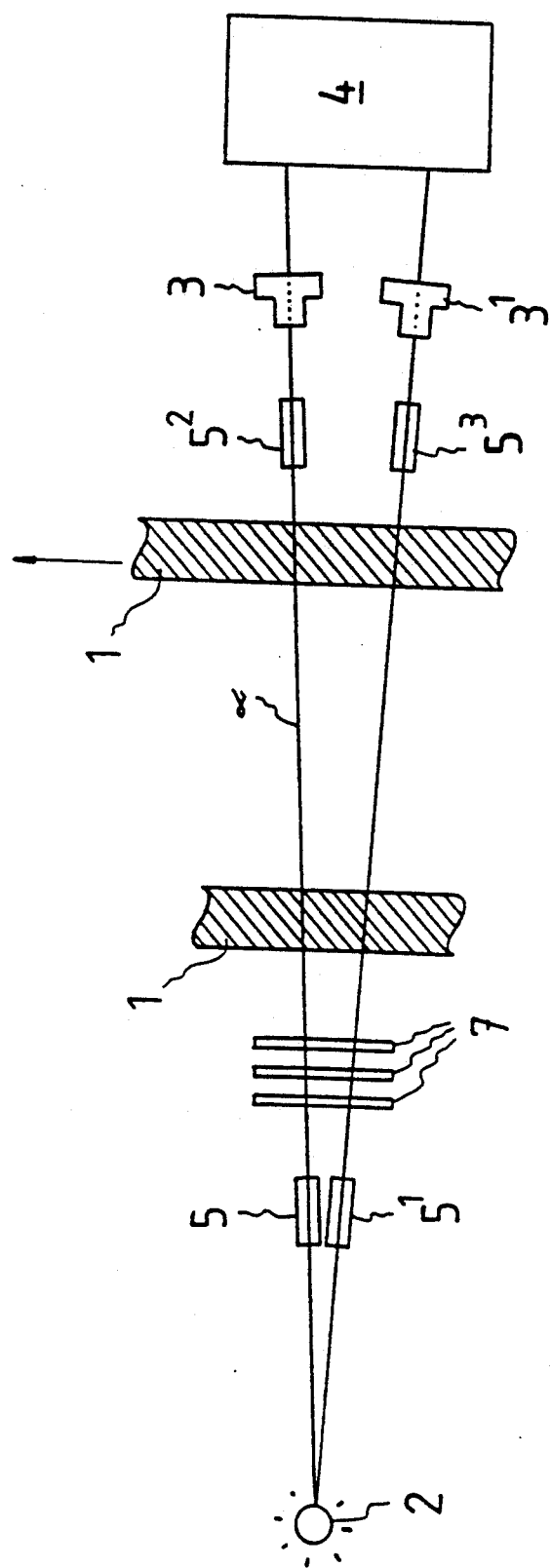

As shown in FIG. 1, a gamma or x-ray radiation source 2 and two detectors 3,3¹ have been placed on opposite sides of the walls of the pipe 1 to be measured. The detectors have been placed one after the other in the axial direction of the pipe to be measured, and so aligned relative to each other that the beams striking the detectors form equal angles α with the normal on the pipe under observation. The radiation emitted by the radiation source 2 is collineated with the aid of collimators 5,5¹,5²,5³ before the pipe 1, and after the pipe, to form two sharp beams which are directed accurately into the detectors 3,3¹. The radiation may be attenuated with filtering plates 7 in order to adjust the radiation from the radiation source 2 to be appropriate for the detectors 3,3¹.

The measuring apparatus of FIG. 1 is operated as follows. The measuring apparatus is moved in the axial direction of the pipe 1, the radiations from the radiation source 2 traversing both walls of the pipe. If the pipes are of uniform thickness and faultless, the signals going to the output device 4 are similar and the output device gives out no signals in a null balance measurement.

Figure 4:
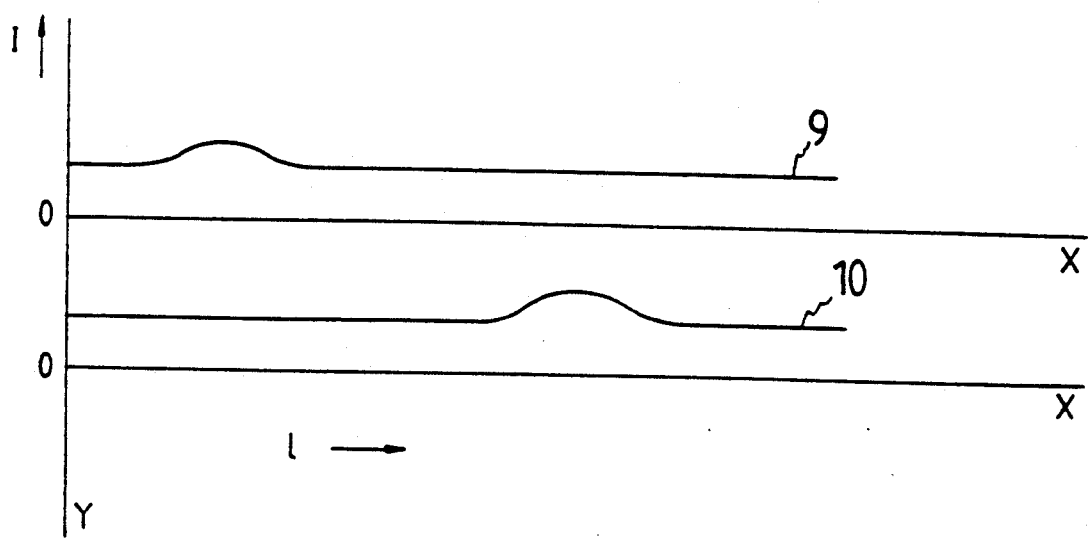
FIG. 4 illustrates the radiation intensities measured by the detectors.

In FIG. 4, the radiation intensity I has been plotted on the y axis and the pipe length 1 in the direction of movement, on the x axis. The curve 9 represents the signal from detector 3 and the curve 10 that from detector 3¹ when the pipe is moved relative to the measuring apparatus. When the pipe or the measuring apparatus is moved relative to the other, the intensity of the radiation changes if there are faults or other changes in the pipe walls. A rise or descent in intensity, i.e., increase or decrease of the radiation passing through the pipe, indicates the wall thickness of the pipe. The measuring range is linear in the measuring direction in the axial direction of the pipe. The measuring speed, when the measuring apparatus is being moved, depends on the detectors, and it may be such that the measurement can even be made at a walking pace.

Referring to FIG. 4, if one of the pipe walls presents, for instance, a thinned spot, the first sign of this fault is received from the first beam, which is absorbed in the pipe structure in a different manner at the fault from that experienced at a faultless point. The x axis representing the pipe length gives information as to the location of the fault in the pipe. As the measuring apparatus is moved on, a similar fault signal is obtained from the other beam, whereby it is seen from the spacing of the fault signals in the x direction, on which of the two pipe walls the fault is located. This observation is based on the circumstance that the beams pass through the pipe at an angle against each other, due to which they pass through the different pipe walls with a different mutual spacing.

Figure 2:
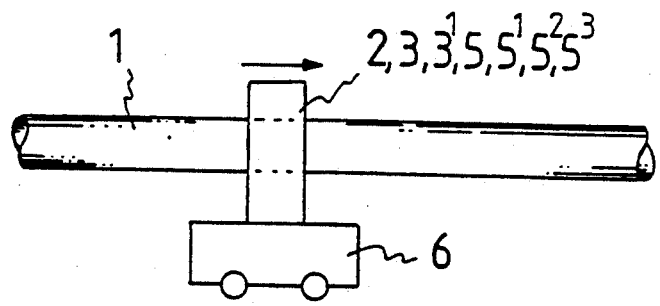

In the embodiment of FIG. 2, the radiation source 2 and the detectors 3,3¹ have been mounted on a transport means 6 by the aid of which the apparatus can be moved relative to the pipe 1 in the axial direction of the pipe, when a measurement is in progress.

Figure 3:
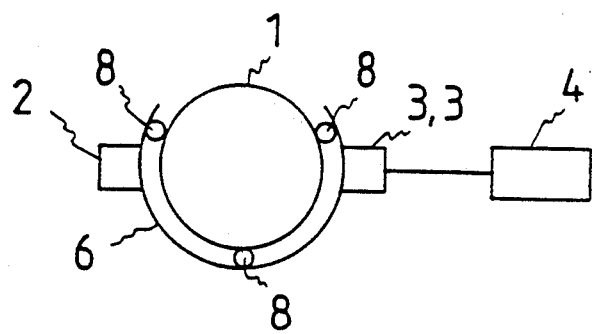
FIG. 3 shows the example of FIG. 2, seen from another viewing angle.

As shown in FIG. 3, around the pipe has been provided a transport means 6, consisting of an arc which is ¾ of the pipe's circumference and which is centrally braced against the pipe with three supporting legs carrying wheels 8. The arc carries, on opposite sides of the pipe, one radiation source and two detectors, one after the other in the axial direction of the pipe. The detectors are aligned to be at an angle e.g. about 3° against the normal on the pipe, and spaced at 10 to 20 mm. The radiation is directed through the apertures of collimators located before the pipe, accurately into the apertures of two collimators on the other side in conjunction with the detectors, and further into the detectors, one specific beam into each. The radiation is attenuated in case of need with filtering plates for ascertaining the wall thickness and good functioning of the detectors. The detector signals are electrically amplified by methods known in the art, when needed to suit the plotter, each channel separately by itself, whereby the thickness will be readable once the apparatus has been calibrated.

The measuring apparatus of the invention can be employed in measuring the faults of various kinds of pipelines, such as faults in the pipe walls, foreign objects present in the pipes, and clogged pipes. The faults in the pipe walls can also be measured without removing the lagging, making the measurement through the lagging.

The invention is not confined to the foregoing examples: its embodiments may vary within the scope of the claims following below.

I claim:

1. Procedure for measuring and locating faults in a pipe, characterized in that through the walls of the pipe are directed two collimated beams traversing the pipe and directed at an angle relative to each other, the beams are moved, one trailing the other, relative to the pipe in the measuring direction, the intensities of the beams that have passed through the both walls of the pipe are measured, and the locations of the faults in the walls of the pipe are determined by comparing the distance in the measuring direction between the signals derived from the beams and the distance between the beams at both traversing points.

2. Procedure according to claim 1, characterized in that the measurement is carried out as a null balance measurement so that the measuring apparatus gives a measuring signal only when the intensities of the beams differ.

3. Procedure according to claim 1, characterized in that when making a measurement the pipe and the measuring apparatus are moved relative to each other in the axial direction of the pipe.

* * * * *